(12) United States Patent
Blake et al.

(10) Patent No.: US 11,986,297 B2
(45) Date of Patent: May 21, 2024

(54) ATMOSPHERIC-BALANCED VACUUM FOR BLOOD GAS SAMPLE STABILIZATION WITH AN EVACUATED CONTAINER

(71) Applicant: Becton, Dickinson and Company, Franklin Lakes, NJ (US)

(72) Inventors: Alexander James Blake, Ridgewood, NJ (US); Sylvine Raverdy-Wilson, River Edge, NJ (US); Adam Edelhauser, Kinnelon, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 793 days.

(21) Appl. No.: 17/056,874

(22) PCT Filed: Jun. 13, 2019

(86) PCT No.: PCT/US2019/037017
§ 371 (c)(1),
(2) Date: Nov. 19, 2020

(87) PCT Pub. No.: WO2019/241537
PCT Pub. Date: Dec. 19, 2019

(65) Prior Publication Data
US 2021/0219889 A1 Jul. 22, 2021

Related U.S. Application Data

(60) Provisional application No. 62/684,800, filed on Jun. 14, 2018.

(51) Int. Cl.
*A61B 5/15* (2006.01)
*A61B 5/145* (2006.01)
(Continued)

(52) U.S. Cl.
CPC .... *A61B 5/150274* (2013.01); *A61B 5/14542* (2013.01); *A61B 5/150351* (2013.01);
(Continued)

(58) Field of Classification Search
CPC .......... A61B 5/150274; A61B 5/14542; A61B 5/150351; A61B 5/154; A61B 5/150755;
(Continued)

(56) References Cited

U.S. PATENT DOCUMENTS 4,936,314 A 6/1990 Kasal et al.
5,230,427 A 7/1993 Betts et al.
(Continued)

FOREIGN PATENT DOCUMENTS

AU 1996083 A 4/1984
CN 101932386 A 12/2010
(Continued)

*Primary Examiner* — Matthew Kremer
*Assistant Examiner* — Jonathan Drew Moroneso
(74) *Attorney, Agent, or Firm* — The Webb Law Firm

(57) ABSTRACT

A biological liquid collection device designed to draw blood using an "atmospheric-balanced vacuum" to ensure the blood is exposed to the sample atmospheric partial pressure oxygen and partial pressure carbon dioxide levels as found in standard arterial blood gas syringes, resulting in blood gas sample stabilization during collection and a superior vacuum shelf-life by reducing the gas permeation rate through the plastic tube. The biological liquid collection device comprises a collection module for receiving a biological liquid sample, an evacuated container having an open end and a closed end wherein the evacuated container contains the collection module therein, and a closure for closing the open end of the evacuated container. The evacuated container comprises a gas composition that is substantially equal to the gas composition of the atmosphere outside of the evacuated (Continued)

container. A method for forming the atmospherically balanced vacuum collection device is also provided.

26 Claims, 12 Drawing Sheets

(51) Int. Cl.
- *A61B 5/154* (2006.01)
- *B01L 3/00* (2006.01)
- *A61B 5/153* (2006.01)

(52) U.S. Cl.
CPC .......... *A61B 5/154* (2013.01); *B01L 3/50825* (2013.01); *A61B 5/145* (2013.01); *A61B 5/15* (2013.01); *A61B 5/153* (2013.01); *B01L 3/50* (2013.01); *B01L 3/5082* (2013.01); *B01L 2200/06* (2013.01); *B01L 2200/0684* (2013.01); *B01L 2300/04* (2013.01); *B01L 2300/044* (2013.01); *B01L 2300/046* (2013.01); *B01L 2300/14* (2013.01)

(58) Field of Classification Search
CPC ....... A61B 5/15003; A61B 5/145; A61B 5/15; A61B 5/153; B01L 3/50825; B01L 2200/0684; B01L 2300/044; B01L 2300/046; B01L 2300/14; B01L 2300/047; B01L 2300/048; B01L 3/50; B01L 3/5082; B01L 2200/06; B01L 2300/04

See application file for complete search history.

(56) References Cited

U.S. PATENT DOCUMENTS

| | | | |
|---|---|---|---|
| 5,683,771 A | 11/1997 | Tropsha | |
| 8,206,916 B2 | 6/2012 | Stordeur et al. | |
| 8,273,312 B2 | 9/2012 | Porat et al. | |
| 9,061,280 B2 * | 6/2015 | Tanaami | B01L 3/505 |
| 9,427,707 B2 | 8/2016 | Montagu et al. | |
| 9,636,062 B2 | 5/2017 | Holmes et al. | |
| 9,649,061 B2 | 5/2017 | Ivosevic et al. | |
| 9,873,117 B2 | 1/2018 | Ivosevic et al. | |
| 2002/0049391 A1 | 4/2002 | Kuracina et al. | |
| 2003/0045857 A1 | 3/2003 | Dubrowny et al. | |
| 2004/0043505 A1 | 3/2004 | Walenciak et al. | |
| 2005/0065454 A1 | 3/2005 | Manoussakis | |
| 2009/0162587 A1 | 6/2009 | Wilkinson et al. | |
| 2009/0162941 A1 * | 6/2009 | Winkler | B01L 3/50825 436/180 |
| 2012/0123297 A1 * | 5/2012 | Brancazio | A61B 5/150732 600/576 |
| 2014/0120606 A1 | 5/2014 | Wolters et al. | |
| 2014/0308165 A1 | 10/2014 | Marchiarullo et al. | |
| 2014/0308409 A1 * | 10/2014 | Savur | B65D 81/2076 426/118 |
| 2015/0098084 A1 | 4/2015 | Felts et al. | |
| 2016/0081606 A1 | 3/2016 | Russ et al. | |
| 2016/0367177 A1 | 12/2016 | Edelhauser et al. | |
| 2019/0015561 A1 | 1/2019 | Wills et al. | |
| 2019/0076074 A1 * | 3/2019 | Bullington | A61B 5/150946 |

FOREIGN PATENT DOCUMENTS

| | | |
|---|---|---|
| CN | 102225738 A | 10/2011 |
| CN | 203935192 U | 11/2014 |
| CN | 108138316 A | 6/2018 |
| DE | 4222397 A1 | 1/1994 |
| EP | 1834582 A1 | 9/2007 |
| JP | H8119653 A | 5/1996 |
| JP | H09164128 A | 6/1997 |
| JP | 2011027470 A | 2/2011 |
| JP | 2016501742 A | 1/2016 |
| JP | 2017531782 A | 10/2017 |
| WO | 9855529 A1 | 10/1998 |
| WO | 2014070514 A1 | 5/2014 |
| WO | 2016145057 A1 | 9/2016 |
| WO | 2018231960 A1 | 12/2018 |

* cited by examiner

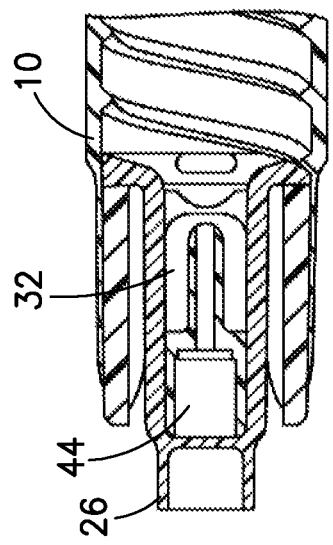
FIG.3A
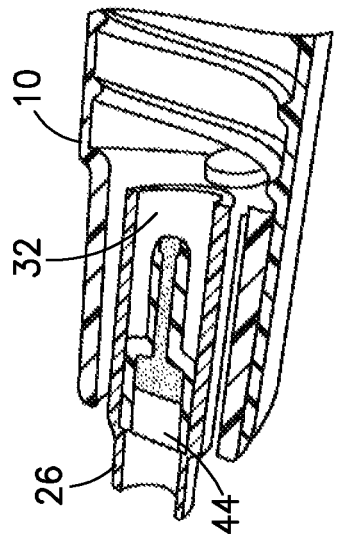
FIG.3B
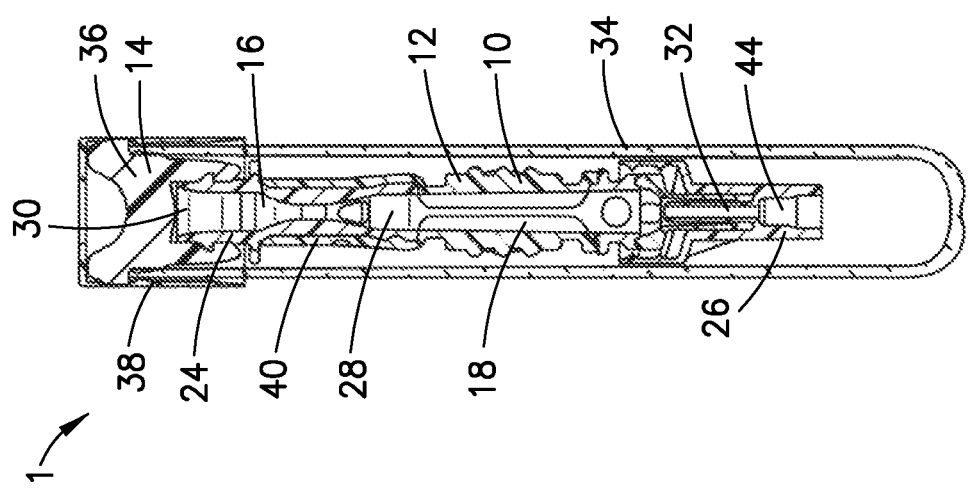
FIG.2
FIG.1

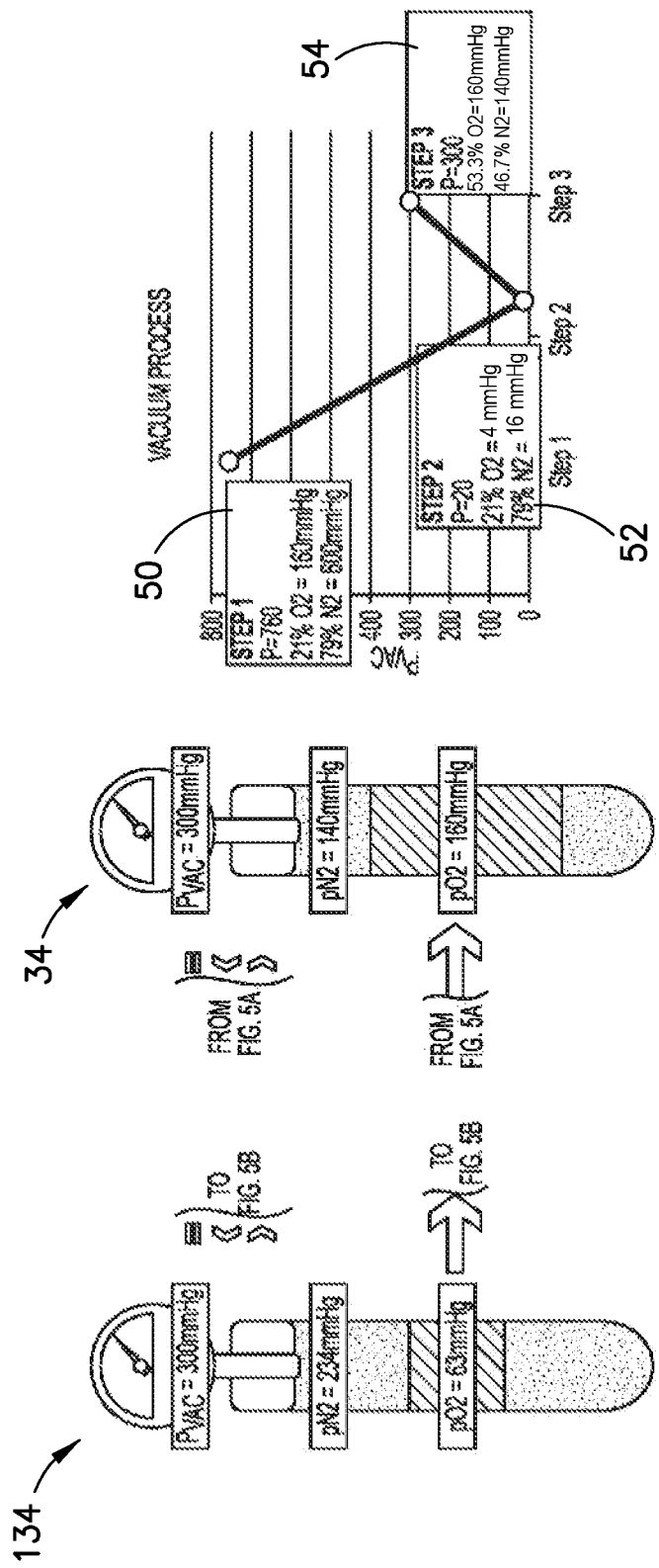

ATMOSPHERIC-BALANCED VACUUM FOR BLOOD GAS SAMPLE STABILIZATION WITH AN EVACUATED CONTAINER

CROSS-REFERENCE TO RELATED APPLICATIONS

This application is the United States national phase of International Application No. PCT/US2019/037017 filed Jun. 13, 2019, and claims priority from and claims the benefit of U.S. Provisional Application Ser. No. 62/684,800, filed Jun. 14, 2018, and entitled, "ATMOSPHERIC-BALANCED VACUUM FOR BLOOD GAS SAMPLE STABILIZATION WITH AN EVACUATED CONTAINER" the entire disclosures of which are hereby incorporated by reference in their entirety.

BACKGROUND OF THE INVENTION

Field of the Invention

The invention relates, in general, to a collection device and a method of making an atmospheric balanced fluid collection device for collecting a biological fluid sample, and more particularly, to a blood sample collection device integrated with an evacuated blood collection tube for use in connection with blood gas analysis and even more particularly to a blood sample collection device designed to draw blood using an "atmospheric-balanced vacuum" to ensure the blood is exposed to the sample atmospheric partial pressure oxygen and partial pressure carbon dioxide levels as found in a standard arterial blood gas (ABG) syringe, resulting in blood gas sample stabilization during collection.

A 1 mL-3 mL syringe-based platform is commonly accepted for blood gas laboratory tests. Current blood gas devices fall within two categories based on the filling methods employed (1) plunger-user assisted and (2) vented-blood pressure assisted. These syringe configurations typically require the user to follow a protocol that involves air purging, capping/sealing, and anticoagulant mixing steps to ensure blood sample quality isn't compromised for analysis in the diagnostic instruments. Besides the complicated multistep workflow, conventional blood collection syringes significantly elevate the safety risk for blood exposure during the air burp and capping procedure.

A recent device for blood collection for collecting small samples of blood and dispensing a portion of the sample into a device intended or designed to analyze the sample, such as point-of-care or a near-patient testing device is disclosed in U.S. Pat. No. 9,649,061, the entirety of which is incorporated herein by reference. The blood sample collection device disclosed therein is integrated within an evacuated container, such as a BD Vacutainer® blood collection tube, owned by Becton, Dickinson, and Company, the assignees of the present invention. Use of this device allows for blood sample collection and dispensing for point-of-care applications which incorporates conventional automatic blood draw and includes a novel controlled sample dispensing capability while minimizing exposure risk. When blood fills a conventional Vacutainer® tube, the gas composition dissolved and bound to hemoglobin in the blood ($O_2$, $N_2$, $CO_2$) is exposed to a gas mixture in the tube where each respective gas mixture component has its own partial pressure. The total pressure in the tube is the sum of the partial pressure of each individual gas ($Ptube=PO_2+PCO_2+PN_2$) as demonstrated by Dalton's law of partial pressures. This fundamental property of gases dictates a traditional tube vacuum pressure of 300 mmHg, respectively. In comparison, normal atmospheric gas composition has an oxygen partial pressure of 160 mmHg at atmospheric pressure, 760 mmHg (at sea level). This standard vacuum process creates an environment that exposes blood to a larger partial pressure gradient ($\Delta P$) for both oxygen and carbon dioxide in a conventional Vacutainer® tube in comparison to a syringe that can then lead to blood gas bias. As a result, gases can come out of solution (blood), as determined by the equilibrium between the undissolved gas in the vacuum tube and the gas dissolved in the blood.

There is need in the art for an atmospheric-balanced vacuum tube architecture that reduces blood gas bias and enables stable blood gas levels during blood vacuum draws using conventional blood collection sets. There is also a need in the art for an atmospheric-balanced vacuum tube architecture that provides a superior vacuum shelf-life by reducing the gas permeation rate through the plastic tube. There is a further need in the art for an atmospheric-balanced conventional specimen collection container, such as an evacuated blood collection tube, that provides a superior vacuum shelf-life by reducing the gas permeating rate through the material plastic.

SUMMARY OF THE INVENTION

The key benefits of the arterial blood gas (ABG) atmospheric-balanced vacuum tube of the present disclosure is the reduction in both blood collection workflow steps and blood exposure associated with conventional (ABG) syringe blood collection sets. The device of the present disclosure provides a simplified user workflow as it uses a vacuum drawing method to uniformly mix anticoagulant in a fixed maximum blood sample that is air free. A plug element is located at a fixed position in a tip cap. This plug element is air permeable and liquid impermeable to allow air to be purged as the device fills and subsequently seals off upon blood contact. This atmospheric-balanced vacuum design of the present disclosure allows the removal of a dispenser component from the evacuated tube, which allows a controlled sample dispenser to a diagnostic instrument cartridge or aspiration by/through a probe in a blood gas diagnostic port.

According to one aspect, the invention comprises a biological liquid collection device comprising a collection module for receiving a biological liquid sample, an evacuated container having an open end and a closed end wherein the evacuated container contains the collection module therein, and a closure for closing the open end of the evacuated container. The evacuated container comprises a gas composition that is substantially equal to the gas composition of the atmosphere outside of the evacuated container.

The gas composition within the evacuated container comprises oxygen, nitrogen, and carbon dioxide. The oxygen in the gas composition located within the evacuated container can have a partial pressure that is substantially equal to a partial pressure of atmospheric oxygen outside of the evacuated container. The carbon dioxide in the gas composition located within the evacuated container can also have a partial pressure that is substantially equal to a partial pressure of atmospheric carbon dioxide outside of the evacuated container.

According to one embodiment, the gas composition can comprise approximately 55% oxygen, approximately 43% nitrogen, and approximately 0.1% carbon dioxide. The evacuated container can have a total pressure of 300 mmHg and the oxygen within the gas composition in the evacuated container can have a partial pressure of approximately 160 mmHg. According to another embodiment, the evacuated container can have a total pressure of 300 mmHg and the carbon dioxide within the gas composition in the evacuated container can have a partial pressure of approximately 0.3 mmHg. According to yet another embodiment, the evacuated container can have a total pressure of 300 mmHg and the oxygen within the gas composition in the evacuated container can have a partial pressure of approximately 160 mmHg and the carbon dioxide within the gas composition in the evacuated container can have a partial pressure of approximately 0.3 mmHg. The total pressure of atmospheric air outside of the evacuated container can be approximately 760 mmHg (temperature and altitude dependent) and the oxygen within the gas composition of the outside air has a partial pressure of approximately 160 mmHg and the carbon dioxide within the gas composition of the outside air has a partial pressure of approximately 0.3 mmHg.

The collection module can include a first end having a sample introduction opening, a second end having a sample dispensing opening, a passageway extending between the sample introduction opening and the sample dispensing opening, and a porous plug covering the second end of the housing. The closure is configured to close the sample introduction opening in the collection module and the closure can comprise a pierceable self-sealing stopper. The porous plug can be designed to allow air to pass from the passageway of the collection module while preventing the biological liquid sample to pass therethrough.

According to another aspect, the invention comprises a biological liquid collection device comprising a collection module for receiving a biological liquid sample, an evacuated container containing the collection module therein, and a closure for closing an open end of the evacuated container, wherein the evacuated container comprises a gas composition that has an enriched oxygen content having a partial pressure substantially equal to or greater than a partial pressure of oxygen in air at atmospheric pressure of 760 mmHg outside of the evacuated container. In another configuration, different altitudes may be accounted for in that a variant air pressure less than 760 mmHg may be utilized.

The evacuated container can have a pressure of approximately 300 mmHg and the partial pressure of oxygen within the evacuated container is approximately 160 mmHg. The gas composition can include carbon dioxide and nitrogen and the partial pressure of carbon dioxide within the evacuated container can be approximately 0.3 mmHg and the nitrogen within the evacuated container can be approximately 140 mmHg.

According to one embodiment, the evacuated container has a pressure of approximately 300 mmHg and the partial pressure of oxygen within the evacuated container is greater than 160 mmHg. The gas composition can comprise approximately 55% oxygen. The gas composition can further comprise approximately 43% nitrogen and approximately 0.1% carbon dioxide.

According to yet another aspect, a method of making an atmospheric balanced fluid collection device comprises providing a container having an open end and a closed end defining a chamber, drawing a vacuum within the container to remove most of the gas from within the chamber, back purging the chamber with a gas composition that is proportioned to equal a gas composition of the atmosphere outside of the evacuated container, wherein the back purging of the chamber is conducted until reaching a predetermined vacuum pressure within the container, and closing the open end of the container.

The predetermined partial pressure within the container is 300 mmHg and the gas composition comprises approximately 53.3% oxygen having a partial pressure of approximately 160 mmHg.

The method further comprises placing a fluid collection module within the container, wherein the fluid collection module comprises a first end having a sample introduction opening, a second end having a sample dispensing opening, a passageway extending between the sample introduction opening and the sample dispensing opening, and a porous plug covering the second end of the housing. The porous plug is adapted to allow air to pass from the passageway of the collection module while preventing the biological liquid sample to pass therethrough.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 1 is a front perspective view of a biological liquid collection device having a collection module disposed within an outer housing in accordance with an aspect of the present disclosure;

FIG. 2 is a partial cross-sectional side view of the biological liquid collection device of FIG. 1 in accordance with an aspect of the present disclosure;

FIGS. 3A-3B are enlarged partial cross-sectional side views of FIGS. 1 and 2 showing the porous plug closing the liquid collection chamber in accordance with an aspect of the present disclosure;

FIGS. 5A-5D are schematic diagrams illustrating the evacuated tube and method of forming the atmospherically-balanced evacuated tube in accordance with the present disclosure;

Corresponding reference characters indicate corresponding parts throughout the several views. The exemplifications set out herein illustrate exemplary embodiments of the disclosure, and such exemplifications are not to be construed as limiting the scope of the disclosure in any manner.

DESCRIPTION OF THE INVENTION

Figures 4A, 4B:
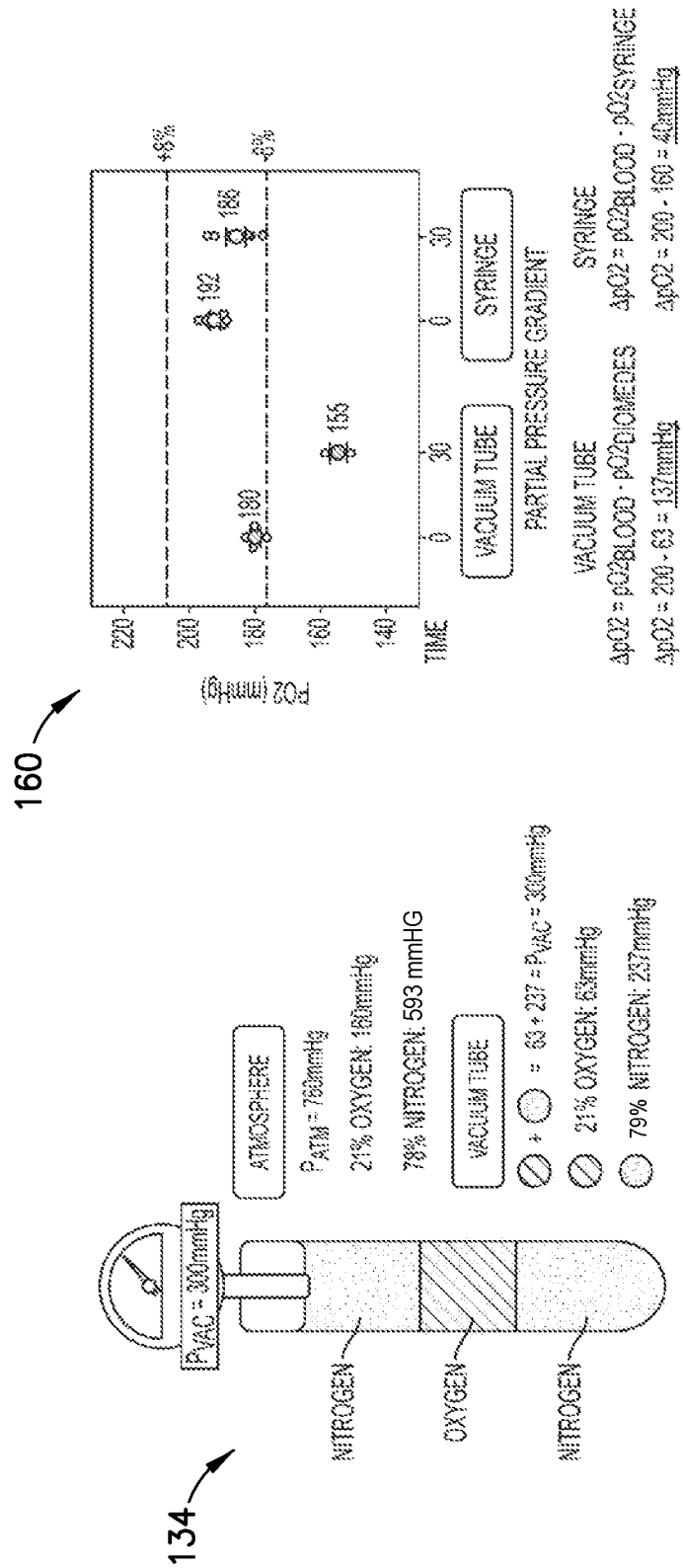
FIGS. 4A-4B are schematic diagrams illustrating blood gas vacuum bias using a standard vacuum process in a conventional Vacutainer® tube in accordance with principles known in the art.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Reference is made to FIGS. 1-2, which show a biological liquid collection device, generally indicated as 1, having a collection module 10 disposed within an outer housing or evacuated container 34 in accordance with an aspect of the present disclosure. The collection module 10 is adapted to receive a biological liquid sample, such as a blood sample, and includes a housing 12, a closure 14, a mixing chamber 16, a holding chamber 18, a cap 26, as shown in FIG. 2, and an activation member 22.

In one embodiment, the housing 12 includes a first end 24, a second end 26, and a passageway 28 extending therebetween and providing fluid communication between the first end 24 and the second end 26 of the housing 12. The passageway 28 has a sample introduction opening 30 at the first end 24 of the housing 12 and a sample dispensing opening 32 at the second end 26 of the housing 12. The mixing chamber 16 and the holding chamber 18 are provided in fluid communication with the passageway 28. The mixing chamber 16 and the holding chamber 18 are positioned such that a biological fluid sample, such as a blood sample, introduced into the sample introduction opening 30 of the passageway 28 will first pass through the mixing chamber 16 and subsequently pass into the holding chamber 18, prior to reaching the sample dispensing opening 32 of the passageway 28. In this way, the blood sample may be mixed with an anticoagulant or other additive provided within the mixing chamber 16 before the stabilized sample is received and stored within the holding chamber 18.

The mixing chamber 16 allows for passive mixing of the blood sample with an anticoagulant or another additive, such as a blood stabilizer, as the blood sample flows through the passageway 28. The internal portion of the mixing chamber 16 may have any suitable structure or form as long as it provides for the mixing of the blood sample with an anticoagulant or another additive as the blood sample passes through the passageway 28. The mixing chamber 16 may include a dry anticoagulant, such as Heparin or EDTA, deposited on or within the mixing chamber 16. The mixing chamber 16 may, for example, include an open cell foam containing dry anticoagulant dispersed within the cells of the open cell foam to promote the effectiveness of the flow-through mixing and anticoagulant uptake.

After passing through the mixing chamber 16, the blood sample may be directed to the holding chamber 18. The holding chamber 18 may take any suitable shape and size to store a sufficient volume of blood necessary for the desired testing, for example 500 µl or less. In the embodiment shown in FIGS. 1 and 2, the holding chamber 18 is defined by a portion of the housing 12 in combination with an elastic sleeve 40 secured about the exterior of the housing 12. The elastic sleeve 40 may be made of any material that is flexible, deformable, and capable of providing a fluid tight seal with the housing 12, including, but not limited to, natural or synthetic rubber, and other suitable elastomeric materials.

With continuing reference to FIGS. 1 and 2 and with further reference to FIGS. 3A and 3B, a porous or vented plug 44 is disposed at the second end 26 of the housing 12 and plugs the sample dispensing opening 32 of the passageway. The construction of the vented plug 44 allows air to pass therethrough and out of the collection module 10 while preventing the blood sample from passing therethrough and may include a hydrophobic filter. The vented plug 44 has selected air passing resistance that may be used to finely control the filling rate of the passageway 28. By varying the porosity of the plug, the velocity of the air flow out of the plug 44, and thus the velocity of the blood sample flow into the collection module 10, may be controlled. If the blood sample flow velocity into the collection module 10 is too fast, hemolysis may occur. If the blood sample flow velocity into the collection module 10 is too slow, sample collection time may be excessive.

A closure 14 is engaged with the first end 24 of the housing 12 to seal the passageway 28. The closure 14 allows for introduction of a blood sample into the passageway 28 of the housing 12 and may include a pierceable self-sealing stopper 36 with an outer shield 38 such as a Hemogard™ cap commercially available from Becton, Dickinson and Company. The closure 14 also secures to the outer housing or evacuated container 34. It can be appreciated that the evacuated container 34 can be any well-known vacuum containing blood collection tube, such as a Vacutainer® blood collection tube commercially available from Becton, Dickinson and Company.

Reference is now made to FIGS. 4A-4B, which schematically illustrate blood gas vacuum bias using a standard vacuum process in a conventional or prior art evacuated container 134, such as a Vacutainer® container, in accordance with principles known in the art. When blood fills a conventional evacuated container 134, the gas composition dissolved and bound to hemoglobin in the blood ($O_2$, $N_2$, $CO_2$) is exposed to a gas mixture in the tube where each respective gas mixture component has its own partial pressure. The total pressure (P) in the container 134 is the sum of the partial pressures (P) of each individual gas ($P_{tube}=PO_2+PCO_2+PN_2$), as demonstrated by Dalton's law of partial pressures. This fundamental property of gases dictates a traditional tube vacuum pressure of 300 mmHg using an atmospheric gas composition (21% $O_2$, 0.04% $CO_2$ and 78% $N_2$) will result in partial pressures of 63, 0.12, and 234 mmHg, respectively. In comparison, normal atmospheric gas composition has an oxygen partial pressure of 160 mmHg at atmospheric pressure, 760 mmHg (at sea level). As indicated by graph 160, as shown in FIG. 4B, the standard vacuum process creates an environment that exposes blood to a larger partial pressure gradient ($\Delta P$) for both oxygen and carbon dioxide in a conventional evacuated container 134 in comparison to a syringe that can then lead to blood gas bias. Henry's law states that the amount of dissolved gas is proportional to its partial pressure in the gas phase. This equilibrium constant shows that the partial pressure of blood gases are directly proportional to the partial pressure of the gas in the tube. As a result, gases in the conventional container 134 as discussed above and shown in FIG. 4A, will come out of solution (blood), as determined by the equilibrium between the undissolved gas in the evacuated container and the gas dissolved in the blood.

Reference is now made to FIGS. 5A-5D, which schematically illustrate the atmospherically balanced liquid evacuated container 34 and method of preparing the atmospheric balanced evacuated tube 34 in accordance with the present disclosure, wherein the evacuated container 34, which contains the collection module 10, comprises a gas composition that is substantially equal to the gas composition of the atmosphere outside of the evacuated container 34. The proposed device balances the fundamental partial pressure composition of oxygen, $O_2$ and carbon dioxide $CO_2$ within the vacuum chamber to that of the atmospheric conditions to provide a blood gas sample equivalent to a standard arterial blood gas ABG syringe (current standard of care). This was accomplished by developing a vacuum assembly procedure where a high vacuum is pulled and then oxygen $O_2$ and carbon dioxide $CO_2$ are backfilled into the chamber until achieving the desired final vacuum level and partial pressures of $O_2$ and $CO_2$. This process is discussed in more detail below in relation to FIG. 5C.

The presently disclosed device and method results in the collection of blood samples into a vacuum chamber or into the evacuated container 34 where blood is exposed to the same atmospheric partial pressure of oxygen ($PO_2$) and partial pressure of carbon dioxide ($PCO_2$) levels found in a standard arterial blood gas syringe, which exposes the blood sample to normal atmospheric air and its respective $PO_2$ and $PCO_2$ levels, as shown in the graph of FIG. 4B. With continuing reference to FIG. 5C, the method for obtaining the atmospherically balanced container 34 of the present disclosure is achieved by starting with a container (step 1, 50) which is at atmospheric pressure, 760 mmHg, comprising a composition of approximately 21% oxygen, $O_2$ and 79% nitrogen, $N_2$ having a partial pressure of nitrogen, $PN_2$ of approximately 600 mmHg and a partial pressure of oxygen $PO_2$ of approximately 160 mmHg. Next, a high vacuum (step 2, 52) is pulled from within the tube to where most of the gas is removed from the chamber 134 so that the tube has a total pressure of approximately 20 mmHg and the composition of the tube is approximately 21% oxygen, $O_2$ having a partial pressure $PO_2$ of approximately 4 mmHg and approximately 79% nitrogen, $N_2$, having a partial pressure $PN_2$ of approximately 16 mmHg. In a final step (step 3, 54) back purging the tube with a deliberately proportioned gas composition of $O_2$, $N_2$, and $CO_2$ until reaching the desired vacuum level of approximately 300 mmHg that coincides with atmospheric partial pressures of $O_2$ and $CO_2$ forming the atmospherically balanced evacuated tube 34, of the disclosure, as shown in FIG. 5B, wherein the composition of the tube is approximately 55% oxygen (or approximately 53.3% $O_2$ and 0.1% $CO_2$) and 46.7% nitrogen and the partial pressure of 53.3% oxygen, $PO_2$ is approximately 160 mmHg, the partial pressure of 46.7% nitrogen, $PN_2$ is approximately 140 mmHg, and the partial pressure of carbon dioxide $CO_2$ is approximately 0.3 mmHg. It can be appreciated that the tube can be back purged such that the partial pressure of oxygen within the evacuated container is greater than 160 mmHg.

Figure 5D:
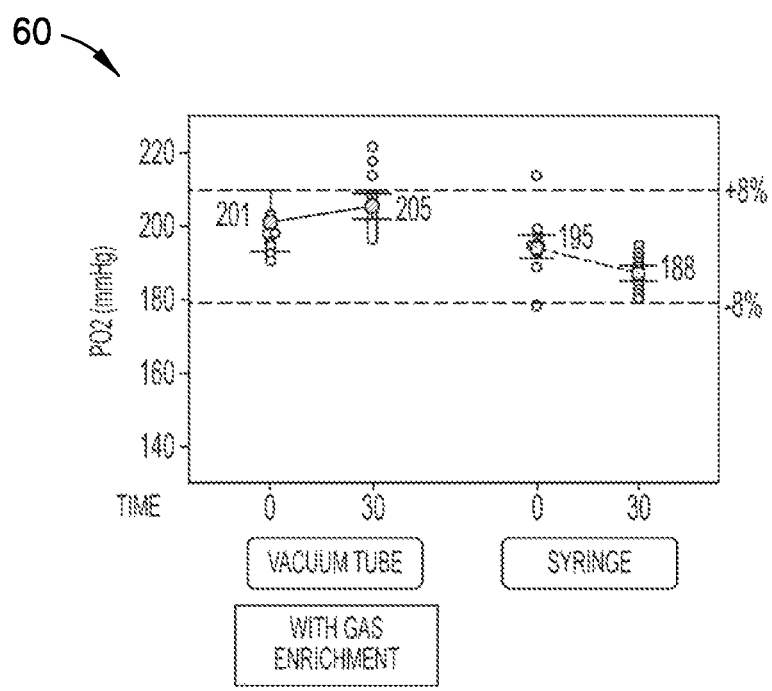

The evacuated container 34 of the present disclosure having a total pressure of 300 mmHg, shown in FIG. 5B differs from the conventional evacuated container 134, shown in FIGS. 4A and 5A having a total pressure of 300 mmHg and partial pressure of nitrogen $PN_2$ of 234 mmHg and a partial pressure of oxygen $PO_2$ of 63 mmHg. As illustrated in the graph 60, shown in FIG. 5D, the partial pressure gradient $\Delta P$ of oxygen $O_2$ between the evacuated container 34 of the invention, in which gas enrichment has been performed, and a syringe are substantially similar.

Atmospheric-balanced partial pressure $PO_2$ and $PCO_2$ vacuum tube architecture enables stable blood gas levels during blood vacuum draws using conventional blood collection sets based on the typical evacuated container systems.

Figure 6:
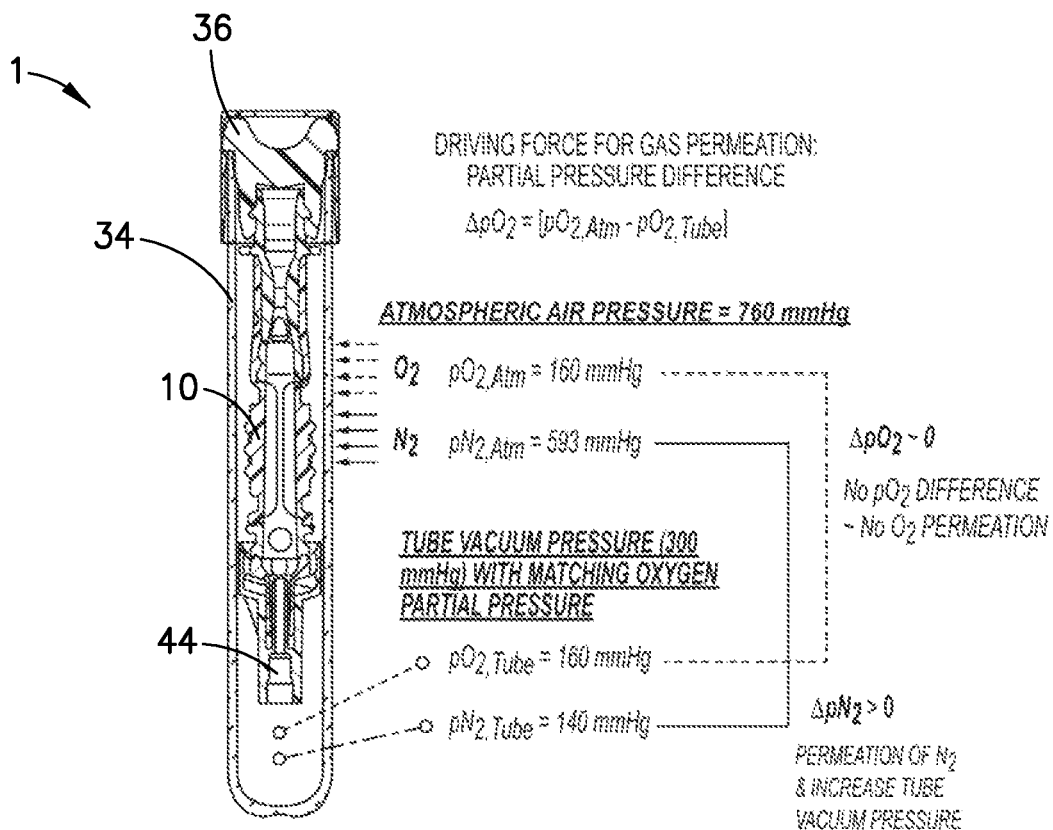
FIG. 6 is a schematic diagram illustrating the principles of tube vacuum shelf-life in accordance with an aspect of the present disclosure.

Vacuum shelf-life loss in the evacuated containers 134 of the prior art is due to gas permeation through the plastic tube, which is driven by the atmospheric and vacuum partial pressure gradient at the plastic barrier as illustrated in FIG. 6. Nitrogen contributes the least to vacuum loss as the permeation factor for oxygen is an order of magnitude higher in polythethylene terethalate (PET), a plastic primarily used in typical evacuated tubes. An atmospheric-balanced vacuum tube architecture provides a superior vacuum shelf-life, as the balanced $PO_2$ and $PCO_2$ gradients are not susceptible to gas permeation. This is due to the fact that by design there is no difference in $PO_2$ and $PCO_2$ pressures inside and outside the container 134 of the prior art. For example, when the total pressure of atmospheric air outside of the evacuated container is 760 mmHg, the oxygen within the gas composition of the outside air has a partial pressure of approximately 160 mmHg and the carbon dioxide within the gas composition of the outside air has a partial pressure of approximately 0.3 mmHg. In the atmospherically balanced evacuated tube 34 of the present disclosure, the oxygen within the gas composition within the tube also has a partial pressure of approximately 160 mmHg and the carbon dioxide within the gas composition within the tube has a partial pressure of approximately 0.3 mmHg. Because the partial pressure of oxygen, $PO_2$ and carbon dioxide, $PCO_2$ are the same inside and outside the tube (homeostasis), there is no pressure exchange and no resultant vacuum loss from the $O_2$ and $CO_2$. This is significant because oxygen, $O_2$ and carbon dioxide, $CO_2$ make up more than 50% of the total vacuum pressure in the atmospheric-balanced evacuated container 34 of the present disclosure, when the vacuum level is at 300 mmHg. The difference in partial pressure of nitrogen, $N_2$ within and outside of the tube can be significantly different, i.e., the partial pressure of nitrogen $PN_2$ within the tube is approximately 140 mmHg and the partial pressure of nitrogen $PN_2$ within the atmosphere outside of the tube is approximately 593 mmHg. This difference in partial pressure can result in a slight increase in the vacuum pressure within the tube due to nitrogen, $N_2$ permeation into the tube because nitrogen has approximately 10× lower permeability vs. oxygen. It is noted herein, that the atmospheric-balancing compositions as described herein could be useful in increasing the shelf-life of any conventional specimen collection container. For example, this atmosphere-balancing technique could be useful for prolonging the shelf-life of plastic blood collection containers, including any kind of evacuated tube. Although this application has particular applicability to arterial blood gas applications, the atmospheric-balancing methodologies described herein can be utilized for any evacuated plastic container.

It can be appreciated that patients exposed to hyperoxia conditions over a prolonged period can experience a higher than normal partial pressure of oxygen that can exceed 500 mmHg. Under these conditions, gas is forced to dissolve in an unbound state in the plasma of blood while a smaller portion is still bound to hemoglobin. During blood gas analysis, these samples can exhibit higher bias levels within the typical 15 minute turn-around times as oxygen in plasma has a high dissolution gas exchange rate combined with the partial pressure gradient when blood is exposed to atmosphere. Hyperoxia (relative to atmospheric $PO_2$ and $PCO_2$) $PO_2$ and $PCO_2$ levels could be used in the vacuum tube architecture to further improve blood gas stability for an oxygen therapy product that isn't susceptible to bias at extremes. This is feasible for ABG blood gas applications as the device design doesn't have a high enough surface area required to positively bias blood gas levels. This would never be possible in a classic ABG syringe.

Figure 7A:
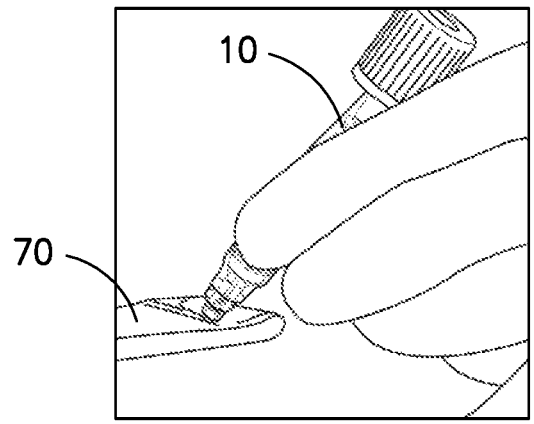
FIGS. 7A-7B are perspective views of dispensing of the blood gas sample into testing devices in accordance with aspects of the present disclosure.
Figure 7B:
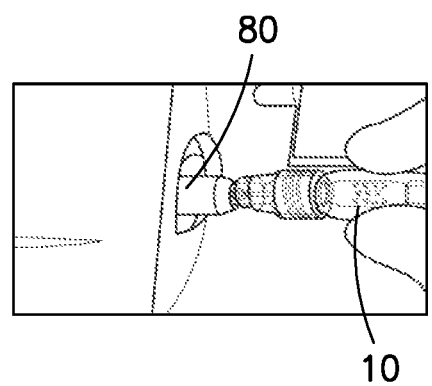

Further, as shown in FIGS. 7A and 7B, the device of the present invention provides improvement in substantial reduction or elimination of air contamination in blood sampling procedures through the use of a preset volume of blood so that upon removal of the collection module 10 from the evacuated tube, the sample that can be consistently delivered by aspiration to a Point of Care (PoC) cartridge 70, FIG. 7A or other ABG diagnostic instrument ports 80, FIG. 7B.

Figure 8:
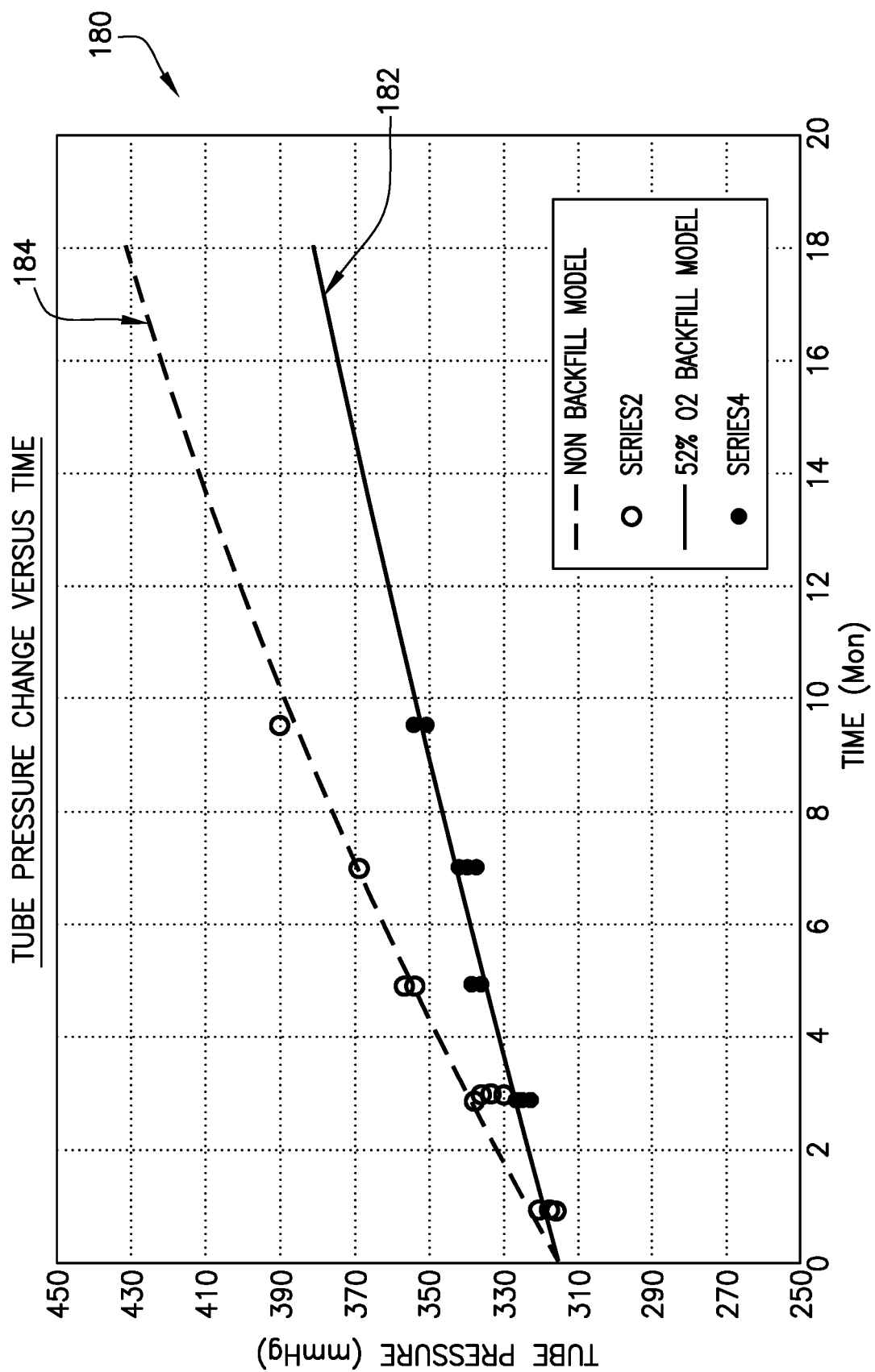
FIG. 8 is a graph showing tube pressure versus time of an oxygen backfilled tube in accordance with the disclosed invention, as well as a non-backfilled tube.
Figure 9:
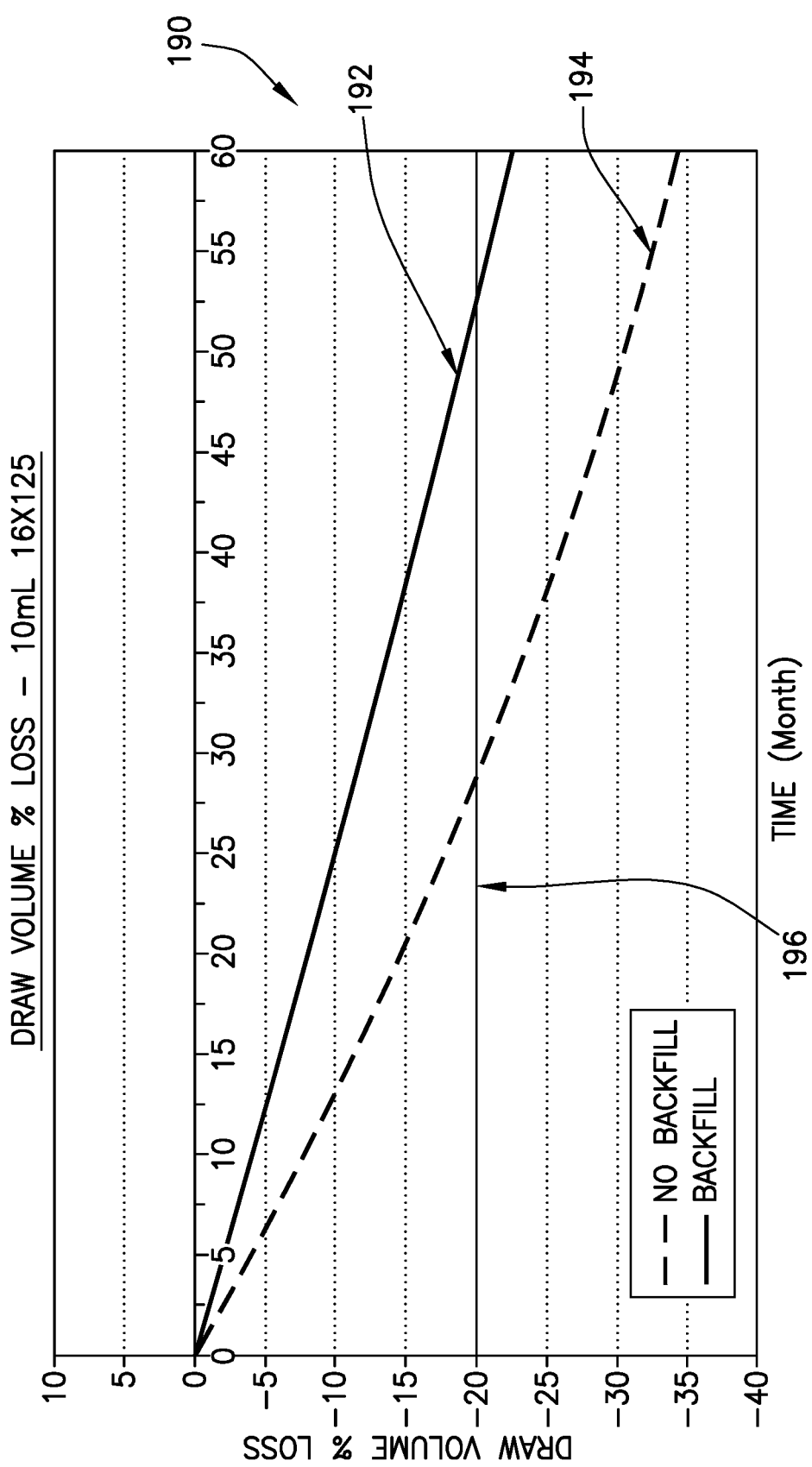
FIG. 9 is a graph showing draw volume percentage loss versus time of a 10 mL 16×125 oxygen backfilled tube in accordance with the disclosed invention, as well as a 10 mL 16×125 non-backfilled tube.
Figure 10:
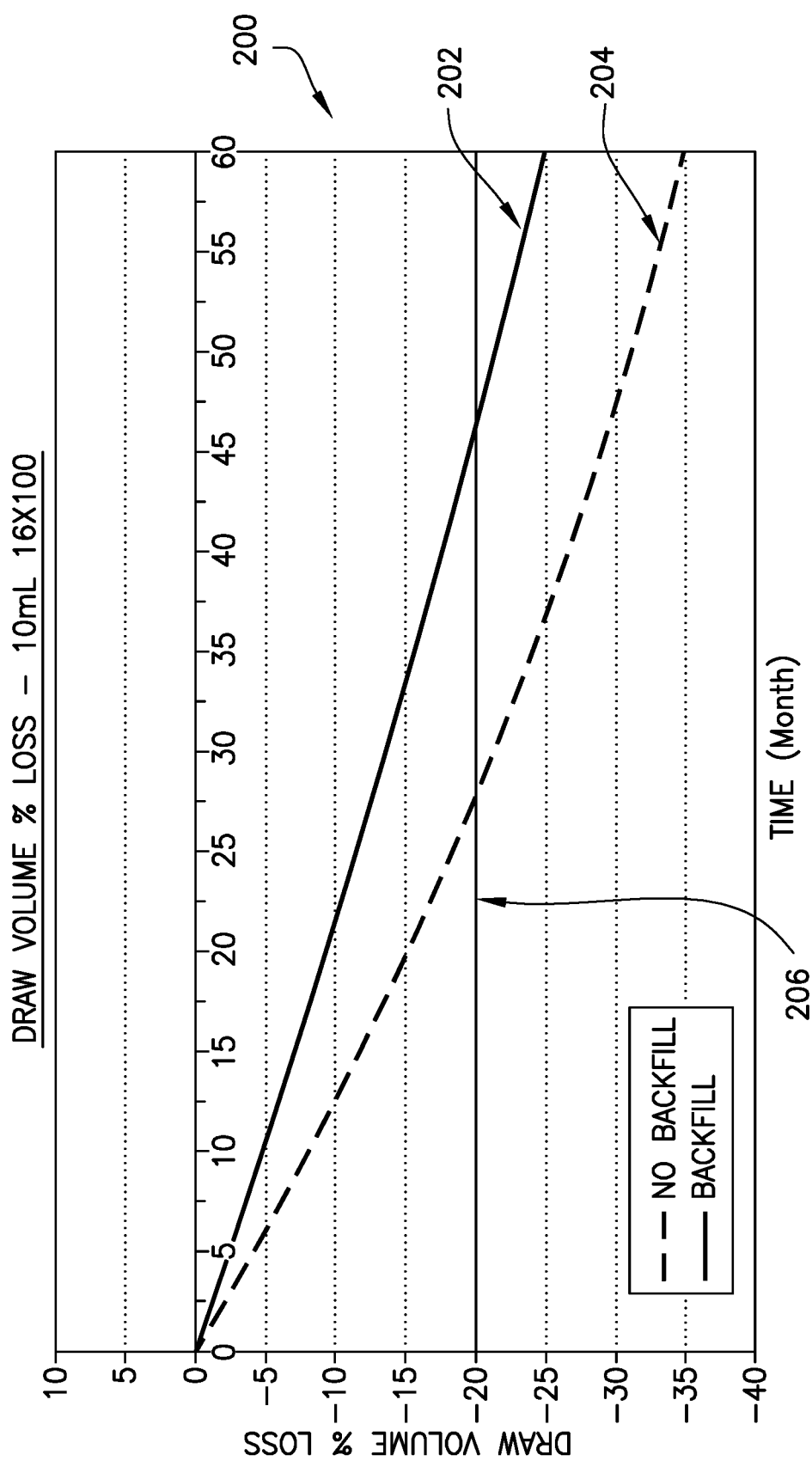
FIG. 10 is a graph showing draw volume percentage loss versus time of a 10 mL 16×100 oxygen backfilled tube in accordance with the disclosed invention, as well as a 10 mL 16×100 non-backfilled tube.
Figure 11:
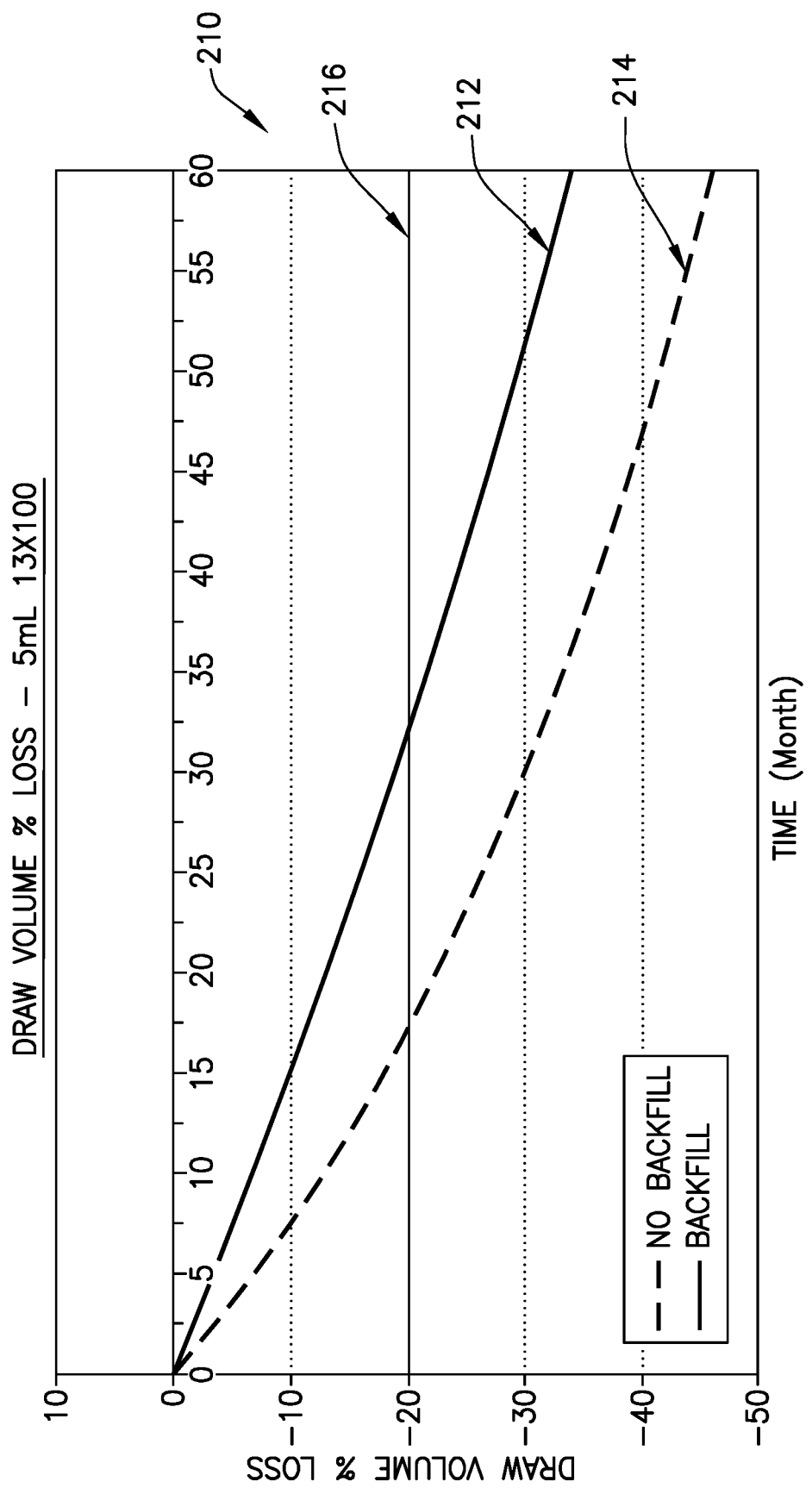
FIG. 11 is a graph showing draw volume percentage loss versus time of a 5 mL 13×100 oxygen backfilled tube in accordance with the disclosed invention, as well as a 5 mL 13×100 non-backfilled tube.
Figure 12:
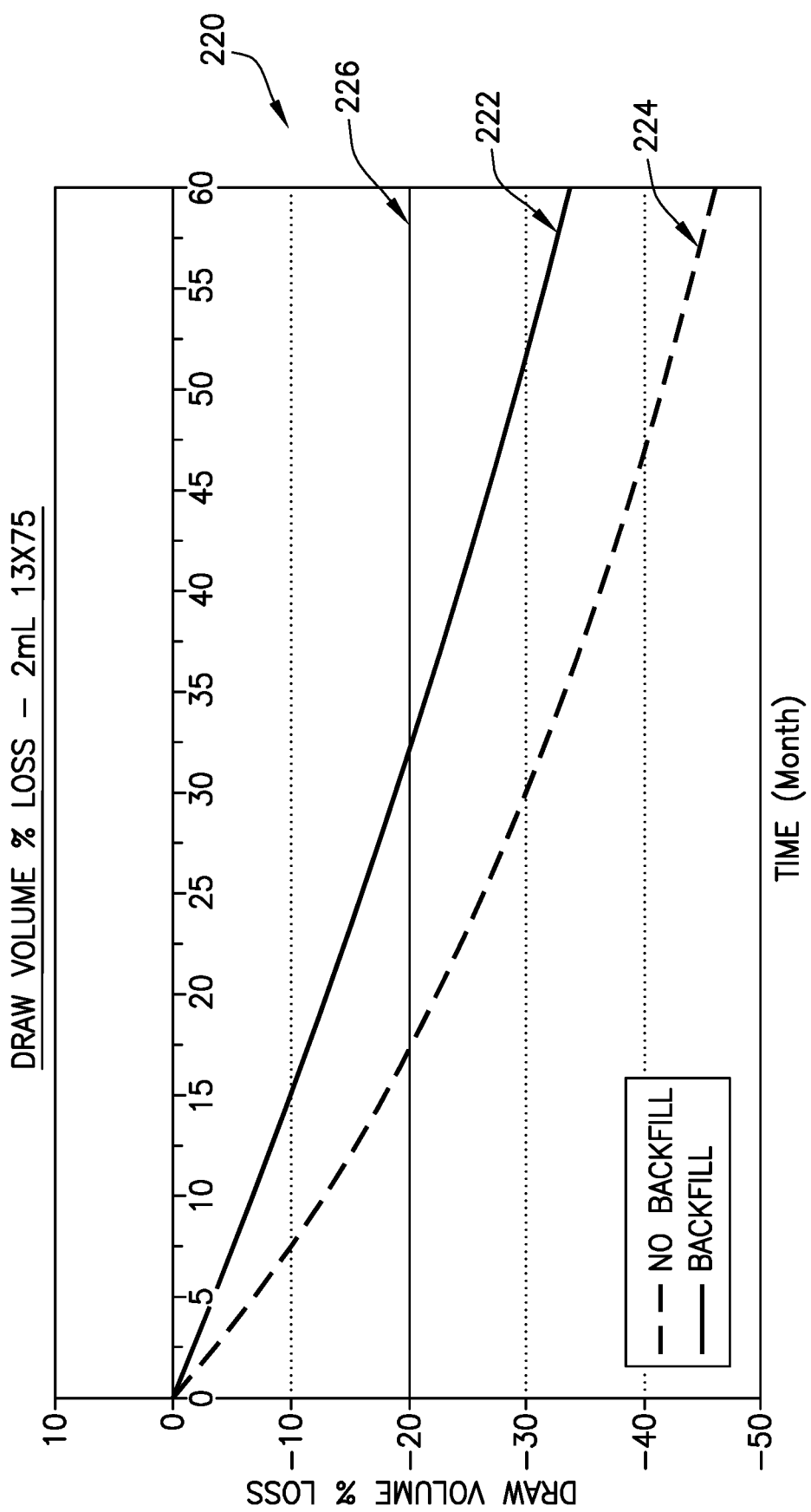
FIG. 12 is a graph showing draw volume percentage loss versus time of a 2 mL 13×75 oxygen backfilled tube in accordance with the disclosed invention, as well as a 2 mL 13×75 non-backfilled tube.
Figure 13:
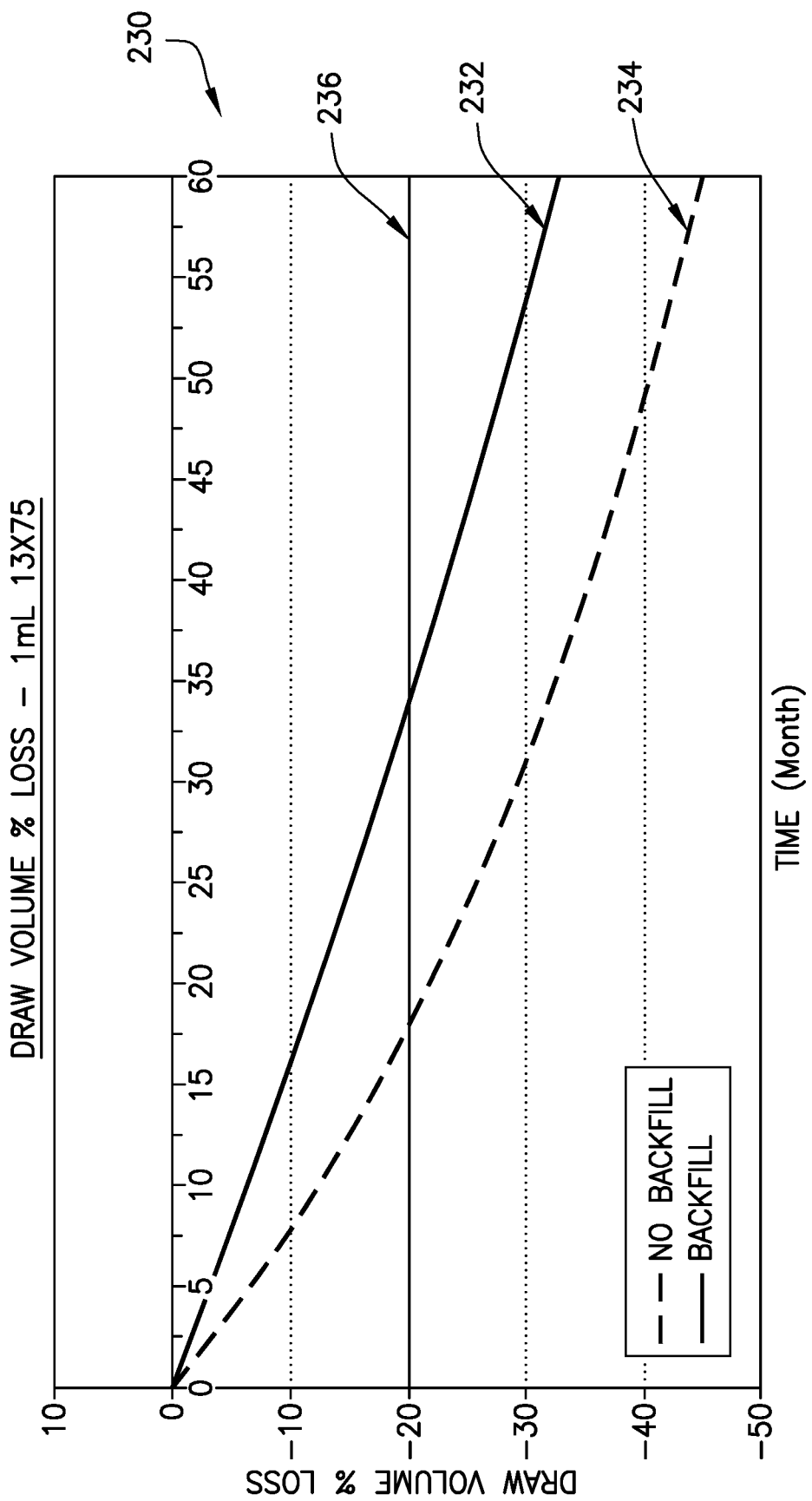
FIG. 13 is a graph showing draw volume percentage loss versus time of a 1 mL 13×75 oxygen backfilled tube in accordance with the disclosed invention, as well as a 1 mL 13×75 non-backfilled tube.

FIG. 8 shows a graph 180 of tube pressure change (e.g., vacuum loss) versus time of an $O_2$ backfilled tube 182 and a non-backfilled tube 184. As shown, data predicts that the 52% $O_2$ backfilled tube 182 will advantageously increase in pressure much more slowly than the non-backfilled tube 184. During testing, evacuated blood collection tubes were tested to verify results. A first group was prepared by removing air, and then backfilling with Oxygen gas until the mixture of gas inside the tube was 52% Oxygen. The other group was prepared by removing air, but the mixture of air was not adjusted from atmospheric air (e.g., 21% $O_2$). The pressure inside the two devices was compared at specific intervals over a period of 10 months. The experimental data, depicted as points in the graph 180, shows that the performance matches a mathematical model. Accordingly, the inventors have discovered that backfilling the tube 182 with a relatively high percentage of $O_2$ improves shelf life by slowing the overall rate of permeability through the tube 182.

FIGS. 9-13 further illustrate the improvement in shelf life for different sized tubes (e.g., 10 mL 16×125, 10 mL 16×100, 5 mL 13×100, 2 mL 13×75, and 1 mL 13×75, respectively) provided by the disclosed concept. More specifically, if a health care professional, e.g., a doctor or a nurse, selects a tube to collect a blood sample, and that tube indicates that it can collect a predetermined quantity of blood (e.g., a 10 mL tube), that professional will expect that the tube will fill up with 10 mL of blood, and if the tube only collects 1 or 5 mL of blood, that will not be acceptable. It is generally known that tubes that are still able to draw within 20% of the volume that they drew when they were first evacuated are still usable. However, once a tube draws less than 80% of its initial draw volume, it is not considered to be usable by professionals taking samples.

FIGS. 9-13 illustrate different graphs 190, 200, 210, 220, 230 of draw volume as a function of time due to the permeability of the tube being tested. As shown in each of the plots, $O_2$ backfilled tubes 192, 202, 212, 222, 232 have been found to take significantly longer to reach a threshold (e.g., a critical 20% threshold 196, 206, 216, 226, 236 wherein the tube can still draw within 20% of the volume that it drew when it was first evacuated, referred to herein as "shelf life") than counterpart non-backfilled tubes 194, 204, 214, 224, 234. As a result, this corresponds to a significantly improved shelf life for the $O_2$ backfilled tubes 192, 202, 212, 222, 232. Specifically, when a container is one of a 10 mL 16×125 tube 192, a 10 mL 16×100 tube 202, a 5 mL 13×100 tube 212, a 2 mL 13×75 tube 222, and a 1 mL 13×75 tube 232, the container has a shelf life of at least 45 months, 40 months, 27 months, 27 months, and 30 months respectively, and preferably at least 52 months, 45 months, 32 months, 32 months, and 34 months, respectively. Moreover, it will be appreciated that in each of the depicted examples, e.g., FIGS. 9-13, the shelf lives of the $O_2$ backfilled tubes 192, 202, 212, 222, 232 have all been found to be increased by a factor of at least 1.5 as a result of being back purged, some having their shelf lives increased by a factor of at least 1.8. That is, the shelf lives of the containers are at least 1.5 times longer, sometimes 1.8 times longer, than they would be without the back purging.

It can be appreciated that an alternative system configuration to the POC architecture is using various evacuated tubes that are assembled using the "atmospheric-vacuum method" for blood gas applications that may require more blood volume. It can also be appreciated that a highly enriched $O_2$ and $CO_2$ gas composition version could be utilized for alternative applications where the sample is much more time susceptible to bias in blood gas analysis in conventional blood gas collection syringes. It is also contemplated herein that the gas composition could alternatively include almost 1% argon as well as other trace gasses.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure that are known or customarily practiced in the art to which this disclosure pertains and which fall within the limits of the appended claims.

The invention claimed is:

1. A biological liquid collection device, comprising:
    a collection module for receiving a biological liquid sample, the collection module having a first end having a sample introduction opening;
    an evacuated container having an open end and a closed end, said evacuated container containing the collection module therein, wherein the first end of the collection module is located adjacent to the open end of the evacuated container; and
    a closure for closing the open end of the evacuated container, wherein the evacuated container comprises a gas composition with a select partial pressure of a targeted gas that is substantially equal to a targeted gas partial pressure of an atmosphere outside of the evacuated container.

2. The biological liquid collection device of claim 1, wherein the evacuated container comprises a gas composition with select partial pressures of targeted gasses that are substantially equal to targeted gas partial pressures of the atmosphere outside of the evacuated container.

3. The biological liquid collection device of claim 1, wherein the gas composition within the evacuated container comprises oxygen, nitrogen, and carbon dioxide.

4. The biological liquid collection device of claim 3, wherein the oxygen in the gas composition located within the evacuated container has a partial pressure that is substantially equal to a partial pressure of atmospheric oxygen outside of the evacuated container.

5. The biological liquid collection device of claim 3, wherein the carbon dioxide in the gas composition located within the evacuated container has a partial pressure that is substantially equal to a partial pressure of atmospheric carbon dioxide outside of the evacuated container.

6. The biological liquid collection device of claim 3, wherein the gas composition comprises approximately 55% oxygen, approximately 43% nitrogen, and approximately 0.1% carbon dioxide.

7. The biological liquid collection device of claim 6, wherein the evacuated container has a total pressure of 300 mmHg and wherein the oxygen within the gas composition in the evacuated container has a partial pressure of approximately 160 mmHg.

8. The biological liquid collection device of claim 7, wherein the carbon dioxide within the gas composition in the evacuated container has a partial pressure of approximately 0.3 mmHg.

9. The biological liquid collection device of claim 8, wherein the oxygen within the gas composition of the atmosphere has a partial pressure of approximately 160 mmHg and the carbon dioxide within the gas composition of the atmosphere has a partial pressure of approximately 0.3 mmHg.

10. The biological liquid collection device of claim 1, wherein the collection module includes, a second end having a sample dispensing opening, a passageway extending between the sample introduction opening and the sample dispensing opening, and a porous plug covering the second end of the collection module.

11. The biological liquid collection device of claim 10, wherein the closure is configured to close the sample introduction opening in the collection module and wherein the closure comprises a pierceable self-sealing stopper.

12. The biological liquid collection device of claim 10, wherein the porous plug is adapted to allow air to pass from the passageway of the collection module while preventing the biological liquid sample to pass therethrough.

13. The biological liquid collection device of claim 1, wherein, when the evacuated container is one of a 10 mL 16×125 tube, a 10 mL 16×100 tube, a 5 mL 13×100 tube, a 2 mL 13×75 tube, and a 1 mL 13×75 tube, the evacuated container has a shelf life of at least 45 months, 40 months, 27 months, 27 months, and 30 months, respectively.

14. A biological liquid collection device comprising:
a collection module for receiving a biological liquid sample the collection module having a first end having a sample introduction opening;
an evacuated container containing the collection module therein, the evacuated container having an open end, wherein the first end of the collection module is located adjacent to the open end of the evacuated container; and
a closure for closing the open end of the evacuated container, wherein the evacuated container comprises a gas composition that has an enriched oxygen content having a partial pressure substantially equal to or greater than a partial pressure of oxygen in air at atmospheric pressure of 760 mmHg outside of the evacuated container.

15. The biological liquid collection device of claim 14, wherein the evacuated container has a pressure of approximately 300 mmHg and wherein the partial pressure of oxygen within the evacuated container is approximately 160 mmHg.

16. The biological liquid collection device of claim 15, wherein the gas composition includes carbon dioxide and nitrogen and wherein a partial pressure of carbon dioxide within the evacuated container is approximately 0.3 mmHg and a partial pressure of the nitrogen within the evacuated container is approximately 140 mmHg.

17. The biological liquid collection device of claim 14, wherein the evacuated container has a pressure of approximately 300 mmHg and wherein the partial pressure of oxygen within the evacuated container is greater than 160 mmHg.

18. The biological liquid collection device of claim 14, wherein the gas composition comprises approximately 55% oxygen.

19. The biological liquid collection device of claim 18, wherein the gas composition further comprises approximately 43% nitrogen and approximately 0.1% carbon dioxide.

20. The biological liquid collection device of claim 14, wherein, when the evacuated container is one of a 10 mL 16×125 tube, a 10 mL 16×100 tube, a 5 mL 13×100 tube, a 2 mL 13×75 tube, and a 1 mL 13×75 tube, the evacuated container has a shelf life of at least 45 months, 40 months, 27 months, 27 months, and 30 months, respectively.

21. A method of making an atmospheric balanced fluid collection device comprising:
providing a container having an open end and a closed end, said container defining a chamber;
placing a fluid collection module within the container, wherein the fluid collection module comprises a first end having a sample introduction opening, the first end being located adjacent to the open end of the container;
drawing a vacuum within the container to remove at least some of the gas from within the chamber;
back purging the chamber with a gas composition that is proportioned to equal a gas composition of an atmosphere outside of the container, wherein the back purging of the chamber is conducted until reaching a predetermined vacuum pressure within the container; and
closing the open end of the container.

22. The method of claim 21, wherein a predetermined partial pressure within the container is 300 mmHg and the gas composition comprises approximately 55% oxygen having a partial pressure of approximately 160 mmHg.

23. The method of claim 21, wherein the fluid collection module comprises a second end having a sample dispensing opening, a passageway extending between the sample introduction opening and the sample dispensing opening, and a porous plug covering the second end of the collection module, said porous plug being adapted to allow air to pass from the passageway of the collection module while preventing a biological liquid sample to pass therethrough.

24. The method of claim 21, wherein a shelf life of the container is increased by a factor of at least 1.5 as a result of the back purging.

25. The method of claim 24, wherein the shelf life of the container is increased by a factor of at least 1.8 as a result of the back purging.

26. The method of claim 21, wherein, when the container is one of a 10 mL 16×125 tube, a 10 mL 16×100 tube, a 5 mL 13×100 tube, a 2 mL 13×75 tube, and a 1 mL 13×75 tube, the container has a shelf life of at least 45 months, 40 months, 27 months, 27 months, and 30 months, respectively.

* * * * *